(12) United States Patent
Behnke

(10) Patent No.: US 8,152,800 B2
(45) Date of Patent: Apr. 10, 2012

(54) ELECTROSURGICAL SYSTEMS AND PRINTED CIRCUIT BOARDS FOR USE THEREWITH

(75) Inventor: Robert Behnke, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 1286 days.

(21) Appl. No.: 11/881,945

(22) Filed: Jul. 30, 2007

(65) Prior Publication Data

US 2009/0036883 A1 Feb. 5, 2009

(51) Int. Cl.
*A61B 18/04* (2006.01)
*A61B 18/18* (2006.01)
*H05K 1/03* (2006.01)

(52) U.S. Cl. .............. 606/34; 606/38; 174/255

(58) Field of Classification Search .......... 606/34, 606/38
See application file for complete search history.

(56) References Cited

U.S. PATENT DOCUMENTS

| | | |
|---|---|---|
| 1,995,526 A | 3/1935 | Wappler |
| 3,699,967 A | 10/1972 | Anderson |
| 3,967,084 A | 6/1976 | Pounds |
| 4,094,320 A * | 6/1978 | Newton et al. ............ 606/35 |
| 4,204,549 A | 5/1980 | Paglione |
| 4,228,809 A | 10/1980 | Paglione |
| 4,311,154 A | 1/1982 | Sterzer et al. |
| 4,375,220 A | 3/1983 | Matvias |
| 4,494,539 A | 1/1985 | Zenitani et al. |
| 4,534,347 A | 8/1985 | Taylor |
| 4,552,143 A | 11/1985 | Lottick |
| 4,580,557 A | 4/1986 | Hertzmann |
| 4,612,940 A | 9/1986 | Kasevich et al. |
| 4,632,127 A | 12/1986 | Sterzer |
| 4,632,128 A | 12/1986 | Paglione et al. |
| 4,638,436 A | 1/1987 | Badger et al. |
| 4,657,015 A | 4/1987 | Irnich |
| 4,672,980 A | 6/1987 | Turner |
| 4,741,348 A | 5/1988 | Kikuchi et al. |
| 4,744,372 A | 5/1988 | Kikuchi et al. |
| 4,747,416 A | 5/1988 | Kikuchi et al. |
| 4,753,248 A | 6/1988 | Engler et al. |
| 4,794,215 A | 12/1988 | Sawada et al. |

(Continued)

FOREIGN PATENT DOCUMENTS

DE 390937 3/1924

(Continued)

OTHER PUBLICATIONS

European Examination Report mailed Nov. 9, 2010 issued by the European Patent Office in co-pending European Application No. 08 013 605.4.

(Continued)

*Primary Examiner* — Linda Dvorak
*Assistant Examiner* — Jaymi Della

(57) ABSTRACT

An electrosurgical system for treating tissue is disclosed. The system includes an electrosurgical generator, a printed circuit board, a generator ground and a patient ground. The printed circuit board is disposed in mechanical cooperation with the electrosurgical generator and includes a plurality of conductive layers. The generator ground includes a first portion and a second portion. The first portion is electro-mechanically connected to a conductive layer of the printed circuit board and the second portion is electro-mechanically connected to another conductive layer of the printed circuit board. The patient ground includes a portion that is at least partially interposed between the first portion of the generator ground and the second portion of the generator ground.

13 Claims, 2 Drawing Sheets

U.S. PATENT DOCUMENTS

| | | |
|---|---|---|
| 4,815,479 A | 3/1989 | Carr |
| 4,860,752 A | 8/1989 | Turner |
| 4,860,770 A | 8/1989 | Kikuchi et al. |
| 4,873,995 A | 10/1989 | Kikuchi et al. |
| 4,884,580 A | 12/1989 | Kikuchi et al. |
| 4,916,275 A | 4/1990 | Almond |
| 4,945,912 A | 8/1990 | Langberg |
| 4,955,377 A | 9/1990 | Lennox et al. |
| 4,967,765 A | 11/1990 | Turner et al. |
| 5,019,076 A | 5/1991 | Yamanashi et al. |
| 5,025,810 A | 6/1991 | Kikuchi et al. |
| 5,033,478 A | 7/1991 | Kikuchi et al. |
| 5,057,106 A | 10/1991 | Kasevich et al. |
| 5,148,814 A | 9/1992 | Kikuchi et al. |
| 5,190,517 A | 3/1993 | Zieve et al. |
| 5,220,927 A | 6/1993 | Astrahan et al. |
| 5,234,004 A | 8/1993 | Hascoet et al. |
| 5,249,121 A | 9/1993 | Baum et al. |
| 5,249,585 A | 10/1993 | Turner et al. |
| 5,275,597 A | 1/1994 | Higgins et al. |
| 5,295,955 A | 3/1994 | Rosen et al. |
| 5,312,400 A | 5/1994 | Bales et al. |
| 5,330,518 A | 7/1994 | Neilson et al. |
| 5,336,220 A | 8/1994 | Ryan et al. |
| 5,342,349 A | 8/1994 | Kaufman |
| 5,344,435 A | 9/1994 | Turner et al. |
| 5,354,325 A | 10/1994 | Chive et al. |
| 5,364,392 A | 11/1994 | Warner et al. |
| 5,383,874 A | 1/1995 | Jackson et al. |
| 5,405,346 A | 4/1995 | Grundy et al. |
| 5,433,740 A | 7/1995 | Yamaguchi |
| 5,571,098 A | 11/1996 | Domankevitz et al. |
| 5,571,154 A | 11/1996 | Ren |
| 5,584,830 A | 12/1996 | Ladd et al. |
| 5,620,480 A | 4/1997 | Rudie |
| 5,628,771 A | 5/1997 | Mizukawa et al. |
| 5,693,082 A | 12/1997 | Warner et al. |
| 5,749,871 A | 5/1998 | Hood et al. |
| 5,800,350 A | 9/1998 | Coppleson et al. |
| 5,800,494 A | 9/1998 | Campbell et al. |
| 5,836,943 A | 11/1998 | Miller, III |
| 5,904,709 A | 5/1999 | Arndt et al. |
| 5,922,013 A | 7/1999 | Fallik |
| 5,944,022 A | 8/1999 | Nardella et al. |
| 5,957,969 A | 9/1999 | Warner et al. |
| 5,961,871 A | 10/1999 | Bible et al. |
| 5,967,976 A | 10/1999 | Larsen et al. |
| 6,016,452 A | 1/2000 | Kasevich |
| 6,019,757 A | 2/2000 | Scheldrup |
| 6,022,346 A | 2/2000 | Panescu et al. |
| 6,032,078 A | 2/2000 | Rudie |
| 6,047,216 A | 4/2000 | Carl et al. |
| 6,052,607 A | 4/2000 | Edwards et al. |
| 6,067,475 A | 5/2000 | Graves et al. |
| 6,068,627 A | 5/2000 | Orszulak et al. |
| 6,071,281 A | 6/2000 | Burnside et al. |
| 6,097,985 A | 8/2000 | Kasevich et al. |
| 6,106,520 A | 8/2000 | Laufer et al. |
| 6,122,551 A | 9/2000 | Rudie et al. |
| 6,134,476 A | 10/2000 | Arndt et al. |
| 6,136,020 A | 10/2000 | Faour |
| 6,142,992 A | 11/2000 | Cheng et al. |
| 6,161,048 A | 12/2000 | Sluijter et al. |
| 6,163,726 A | 12/2000 | Wolf |
| 6,167,313 A | 12/2000 | Gray et al. |
| 6,175,768 B1 | 1/2001 | Arndt et al. |
| 6,179,832 B1 | 1/2001 | Jones et al. |
| 6,181,970 B1 | 1/2001 | Kasevich |
| 6,188,930 B1 | 2/2001 | Carson |
| 6,216,703 B1 | 4/2001 | Manker et al. |
| 6,217,528 B1 | 4/2001 | Koblish et al. |
| 6,222,193 B1 | 4/2001 | Thurston et al. |
| 6,224,421 B1 | 5/2001 | Maturo, Jr. |
| 6,226,553 B1 | 5/2001 | Carl et al. |
| 6,228,079 B1 | 5/2001 | Koenig |
| 6,233,490 B1 | 5/2001 | Kasevich |
| 6,235,020 B1 | 5/2001 | Cheng et al. |
| 6,246,912 B1 | 6/2001 | Sluijter et al. |
| 6,251,128 B1 | 6/2001 | Knopp et al. |
| 6,272,384 B1 | 8/2001 | Simon et al. |
| 6,273,886 B1 | 8/2001 | Edwards et al. |
| 6,275,738 B1 | 8/2001 | Kasevich et al. |
| 6,289,249 B1 | 9/2001 | Arndt et al. |
| 6,293,941 B1 | 9/2001 | Strul et al. |
| 6,296,636 B1 | 10/2001 | Cheng et al. |
| 6,312,391 B1 | 11/2001 | Ramadhyani et al. |
| 6,325,799 B1 | 12/2001 | Goble |
| 6,330,479 B1 | 12/2001 | Stauffer |
| 6,334,074 B1 | 12/2001 | Spertell |
| 6,334,861 B1 | 1/2002 | Chandler et al. |
| 6,347,251 B1 | 2/2002 | Deng |
| 6,366,818 B1 | 4/2002 | Bolmsjo |
| 6,380,815 B1 | 4/2002 | Fehrenbach et al. |
| 6,383,183 B1 | 5/2002 | Sekino et al. |
| 6,402,742 B1 | 6/2002 | Blewett et al. |
| 6,430,446 B1 | 8/2002 | Knowlton |
| 6,451,015 B1 | 9/2002 | Rittman, III et al. |
| 6,461,352 B2 | 10/2002 | Morgan et al. |
| 6,470,217 B1 | 10/2002 | Fenn et al. |
| 6,471,659 B2 | 10/2002 | Eggers et al. |
| 6,477,426 B1 | 11/2002 | Fenn et al. |
| 6,485,486 B1 | 11/2002 | Trembly et al. |
| 6,490,488 B1 | 12/2002 | Rudie et al. |
| 6,494,880 B1 | 12/2002 | Swanson et al. |
| 6,496,736 B1 | 12/2002 | Carl et al. |
| 6,496,738 B2 | 12/2002 | Carr |
| 6,503,191 B1 | 1/2003 | Miller |
| 6,512,956 B2 | 1/2003 | Arndt et al. |
| 6,522,931 B2 | 2/2003 | Manker et al. |
| 6,526,320 B2 | 2/2003 | Mitchell |
| 6,542,767 B1 | 4/2003 | McNichols et al. |
| 6,582,425 B2 | 6/2003 | Simpson |
| 6,582,427 B1 | 6/2003 | Goble et al. |
| 6,592,579 B2 | 7/2003 | Arndt et al. |
| 6,628,990 B1 | 9/2003 | Habib et al. |
| 6,640,139 B1 | 10/2003 | Ueberle |
| 6,666,862 B2 | 12/2003 | Jain et al. |
| 6,671,535 B1 | 12/2003 | McNichols et al. |
| 6,675,050 B2 | 1/2004 | Arndt et al. |
| 6,685,701 B2 | 2/2004 | Orszulak et al. |
| 6,689,131 B2 | 2/2004 | McClurken |
| 6,690,976 B2 | 2/2004 | Fenn et al. |
| 6,723,091 B2 | 4/2004 | Goble et al. |
| 6,725,095 B2 | 4/2004 | Fenn et al. |
| 6,740,079 B1 | 5/2004 | Eggers et al. |
| 6,743,225 B2 | 6/2004 | Sanchez et al. |
| 6,747,218 B2 | 6/2004 | Huseman et al. |
| 6,752,804 B2 | 6/2004 | Simpson et al. |
| 6,771,139 B2 | 8/2004 | Schultheiss et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,796,980 B2 | 9/2004 | Hall |
| 6,823,218 B2 | 11/2004 | Berube |
| 6,847,848 B2 | 1/2005 | Sterzer et al. |
| 6,866,624 B2 | 3/2005 | Chornenky et al. |
| 6,923,804 B2 | 8/2005 | Eggers et al. |
| 6,939,348 B2 | 9/2005 | Malecki et al. |
| 6,944,504 B1 | 9/2005 | Arndt et al. |
| 6,955,675 B2 | 10/2005 | Jain |
| 6,957,108 B2 | 10/2005 | Turner et al. |
| 6,962,586 B2 | 11/2005 | Berube et al. |
| 6,974,463 B2 | 12/2005 | Magers et al. |
| 6,986,764 B2 | 1/2006 | Davenport et al. |
| 6,986,770 B2 | 1/2006 | Hood |
| 6,994,704 B2 | 2/2006 | Qin et al. |
| 7,041,096 B2 | 5/2006 | Malis et al. |
| 7,062,317 B2 | 6/2006 | Avrahami et al. |
| 7,066,933 B2 | 6/2006 | Hagg |
| 7,089,064 B2 | 8/2006 | Manker et al. |
| 7,093,601 B2 | 8/2006 | Manker et al. |
| 7,105,011 B2 | 9/2006 | Auge, II |
| 7,113,832 B2 | 9/2006 | Longo |
| 7,115,121 B2 | 10/2006 | Novak |
| 7,115,126 B2 | 10/2006 | Berube et al. |
| 7,122,031 B2 | 10/2006 | Edwards et al. |
| 7,131,445 B2 | 11/2006 | Amoah |

| | | |
|---|---|---|
| 7,169,144 B2 | 1/2007 | Hoey et al. |
| 7,194,297 B2 | 3/2007 | Talpade et al. |
| 7,195,627 B2 | 3/2007 | Amoah et al. |
| 7,197,363 B2 | 3/2007 | Prakash et al. |
| 7,200,445 B1 | 4/2007 | Dalbee et al. |
| 7,203,556 B2 | 4/2007 | Daners |
| 7,211,081 B2 | 5/2007 | Goble |
| 7,214,224 B2 | 5/2007 | Goble |
| 7,220,260 B2 | 5/2007 | Fleming et al. |
| 7,226,447 B2 | 6/2007 | Uchida et al. |
| 7,278,991 B2 | 10/2007 | Morris et al. |
| 7,306,592 B2 | 12/2007 | Morgan et al. |
| 7,309,336 B2 | 12/2007 | Ashley et al. |
| RE40,156 E | 3/2008 | Sharps et al. |
| 7,422,586 B2 | 9/2008 | Morris et al. |
| 2001/0008966 A1 | 7/2001 | Arndt et al. |
| 2001/0016762 A1 | 8/2001 | Carr |
| 2001/0020178 A1 | 9/2001 | Arndt et al. |
| 2002/0000234 A1 | 1/2002 | Manker et al. |
| 2002/0120261 A1 | 8/2002 | Morris et al. |
| 2002/0156471 A1 | 10/2002 | Stern et al. |
| 2002/0165529 A1 | 11/2002 | Danek |
| 2002/0193849 A1 | 12/2002 | Fenn et al. |
| 2003/0014043 A1 | 1/2003 | Henry et al. |
| 2003/0023238 A1 | 1/2003 | Manker et al. |
| 2003/0055471 A1 | 3/2003 | Fenn et al. |
| 2003/0065317 A1 | 4/2003 | Rudie et al. |
| 2003/0069619 A1 | 4/2003 | Fenn et al. |
| 2003/0144655 A1 | 7/2003 | Panescu |
| 2003/0191513 A1 | 10/2003 | Manker et al. |
| 2003/0195499 A1 | 10/2003 | Mani Prakah et al. |
| 2003/0199863 A1 | 10/2003 | Swanson et al. |
| 2004/0032301 A1 | 2/2004 | Schultheiss et al. |
| 2004/0049254 A1 | 3/2004 | Longo |
| 2004/0122420 A1 | 6/2004 | Amoah |
| 2004/0133254 A1 | 7/2004 | Sterzer et al. |
| 2004/0193147 A1 | 9/2004 | Malecki et al. |
| 2004/0215179 A1 | 10/2004 | Swoyer et al. |
| 2004/0215182 A1 | 10/2004 | Lee |
| 2004/0243120 A1 | 12/2004 | Orszulak et al. |
| 2004/0243200 A1 | 12/2004 | Turner et al. |
| 2005/0038419 A9 | 2/2005 | Arnold et al. |
| 2005/0137662 A1 | 6/2005 | Morris et al. |
| 2005/0143795 A1 | 6/2005 | Habib et al. |
| 2005/0149010 A1 | 7/2005 | Turovskiy et al. |
| 2005/0149012 A1 | 7/2005 | Penny et al. |
| 2005/0182393 A1 | 8/2005 | Abboud et al. |
| 2005/0228370 A1 | 10/2005 | Sterzer et al. |
| 2005/0240239 A1 | 10/2005 | Boveja et al. |
| 2005/0245920 A1 | 11/2005 | Vitullo et al. |
| 2006/0004351 A1 | 1/2006 | Arless et al. |
| 2006/0015161 A1 | 1/2006 | Longo et al. |
| 2006/0015162 A1 | 1/2006 | Edward et al. |
| 2006/0030914 A1 | 2/2006 | Eggers et al. |
| 2006/0106375 A1 | 5/2006 | Werneth et al. |
| 2006/0116673 A1 | 6/2006 | Gauthier et al. |
| 2006/0142753 A1 | 6/2006 | Francischelli et al. |
| 2006/0291178 A1* | 12/2006 | Shih .............. 361/780 |
| 2007/0006435 A1* | 1/2007 | Banerji et al. ........ 29/25.41 |
| 2007/0106297 A1 | 5/2007 | Dumbauld et al. |
| 2007/0123765 A1 | 5/2007 | Hetke et al. |
| 2007/0129721 A1 | 6/2007 | Phan et al. |
| 2007/0219551 A1 | 9/2007 | Honour et al. |
| 2007/0233057 A1* | 10/2007 | Konishi ................ 606/33 |
| 2007/0265612 A1* | 11/2007 | Behnke et al. ........... 606/34 |
| 2008/0004619 A1* | 1/2008 | Malis et al. ............. 606/42 |
| 2008/0071260 A1* | 3/2008 | Shores .................. 606/34 |
| 2008/0287943 A1* | 11/2008 | Weber et al. ............ 606/41 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 500 378 | 1/2005 |
| EP | 1 609 430 | 12/2005 |
| EP | 1 186 274 | 4/2006 |
| EP | 1744354 | 1/2007 |
| EP | 1854423 | 11/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2364461 | 4/1978 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | 94/04220 | 3/1994 |
| WO | WO 9525471 | 9/1995 |
| WO | 00/06246 | 2/2000 |
| WO | 03/034932 | 5/2003 |

OTHER PUBLICATIONS

U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9. 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSurerm™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-1ridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Oapril 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817•825.

S. Humphries Jr. et al., "Finite•Element Codes to Model Electrical Heating and Non L1near Thermal Transport in Biological Media", Proc. ASME HTD-355, 131 (1997).

Urologix, Inc.-Medical Professionals: Targis™ Technology (Date Unknown). "Overcoming the Challenge" located at: <http://www.urologix.com!medicaUtechnology.html> last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation-'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 09151736.7 dated Jun. 5, 2009.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.

* cited by examiner

ELECTROSURGICAL SYSTEMS AND PRINTED CIRCUIT BOARDS FOR USE THEREWITH

BACKGROUND

1. Technical Field

The present disclosure relates to electrically isolating a patient from medical equipment, and more particularly, to electrically isolating a patient ground from a ground of an electrosurgical generator.

2. Background of Related Art

Patients undergoing medical procedures are generally electrically isolated from stray electrical energy of medical equipment connected to the patient. For non-interventional procedures (no medical devices are inserted into the subject), isolation of the patient from the medical device is accomplished by incorporating insulating materials in the construction of surfaces that the patient is likely to touch (e.g. surface coils, patient bed, etc.).

For interventional procedures (medical devices are inserted into the subject), the issue of patient isolation is more complicated since interventional devices themselves are in contact with the patient. This can be especially critical if the invasive device is in contact with electrically-sensitive tissue (e.g., cardiac muscle, brain tissue, etc.). Due to the nature of microwave energy delivery for therapeutic procedures, special requirements exist in isolating a patient, such as the construction of an isolation circuit for use with a microwave generator.

The issue of isolating a patient ground from a generator's ground (i.e., Earth ground) is complex in microwave generators having frequencies above about 500 MHz. In generators with lower frequencies, a transformer may be used to isolate the patient from the generator's ground. As the frequencies get higher, the core loss of the transformer and parasitic elements often overwhelm attempts to transfer energy across an isolation boundary.

Another method of isolating a patient ground from a generator's ground may be with the use of a capacitor. However, with microwave frequencies, the capacitors will add their own losses in terms of reflections and parasitic losses due in part to the voltage isolation requirements of the capacitor.

Accordingly, a need exists for improved devices and methods of isolating a patient ground from a ground of an electrosurgical generator.

SUMMARY

The present disclosure relates to an electrosurgical system for treating tissue. The system includes an electrosurgical generator, a printed circuit board, a generator ground and a patient ground. The printed circuit board is disposed in mechanical cooperation with the electrosurgical generator and includes a plurality of conductive layers. The generator ground includes a first portion and a second portion. The first portion is electro-mechanically connected to a conductive layer of the printed circuit board and the second portion is electro-mechanically connected to another conductive layer of the printed circuit board. The patient ground includes a portion that is at least partially interposed between the first portion of the generator ground and the second portion of the generator ground.

The present disclosure also relates to a printed circuit board for use with a microwave generator. The printed circuit board includes a first conductive layer, a second conductive layer, a third conductive layer, a first dielectric layer, a second dielectric layer and a microstrip. The first conductive layer is configured for electro-mechanical engagement with a first portion of a generator ground. The second conductive layer is configured for electro-mechanical engagement with a portion of a patient ground. The third conductive layer is configured for electro-mechanical engagement with a second portion of the generator ground. The first dielectric layer is interposed at least partially between the first conductive layer and the second conductive layer. The second dielectric layer is interposed at least partially between the second conductive layer and the third conductive layer. The microstrip is disposed in mechanical cooperation with a surface of the printed circuit board.

DESCRIPTION OF THE DRAWINGS

Embodiments of the presently disclosed ground isolation systems are disclosed herein with reference to the drawings, wherein.

DETAILED DESCRIPTION OF EMBODIMENTS

Figure 1:
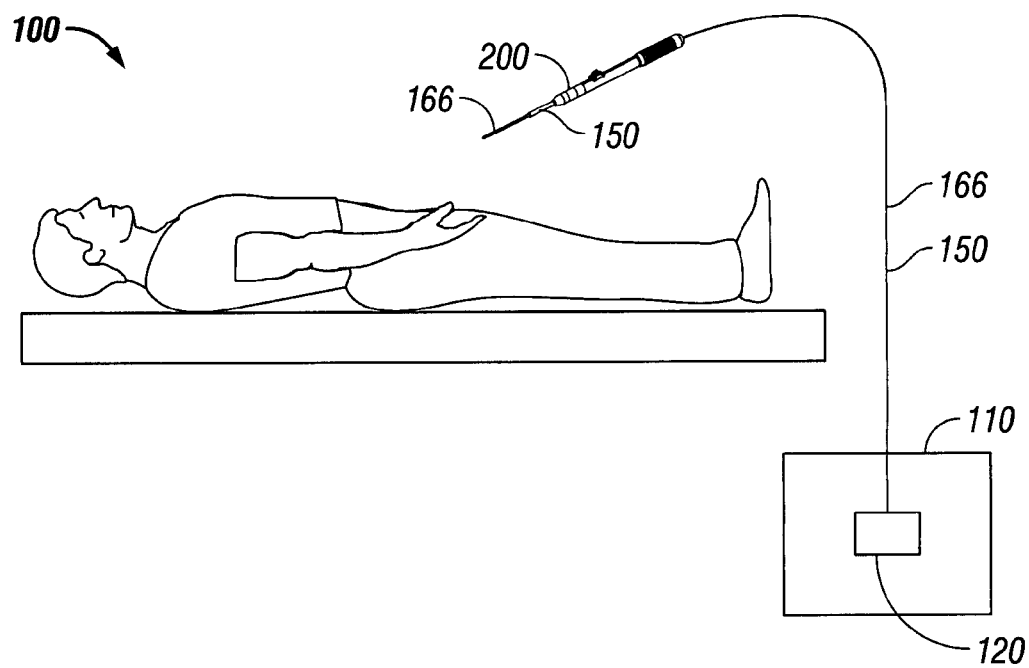
FIG. 1 is a schematic view of an electrosurgical system in accordance with an embodiment of the present disclosure.

Embodiments of the presently disclosed electrosurgical systems and components thereof are described in detail with reference to the drawings, in which like reference numerals designate identical or corresponding elements in each of the several views.

An electrosurgical system, including, for example, a microwave ablation system, for treating tissue in accordance with the present disclosure is referred to in the figures as reference numeral 100. Referring initially to FIG. 1, electrosurgical system 100 includes an electrosurgical generator 110 having a printed circuit board 120 disposed in electro-mechanical cooperation therewith. Electrosurgical system 100 may also include a surgical instrument 200 (e.g., a microwave ablation device).

Figure 2:
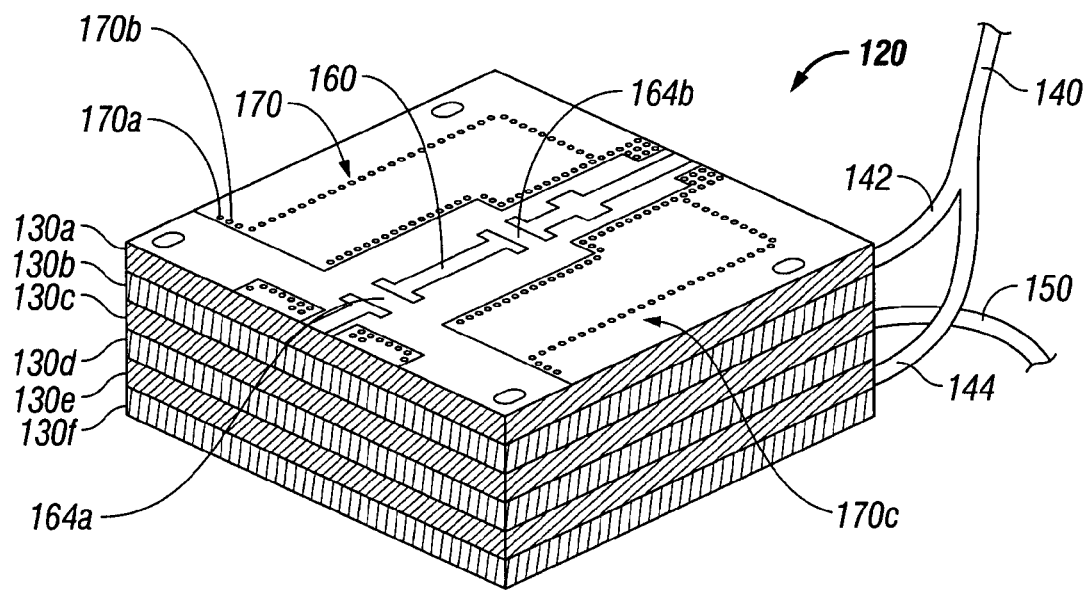
FIG. 2 is a schematic perspective view of a printed circuit board for use with the electrosurgical system of FIG. 1.
Figure 3:
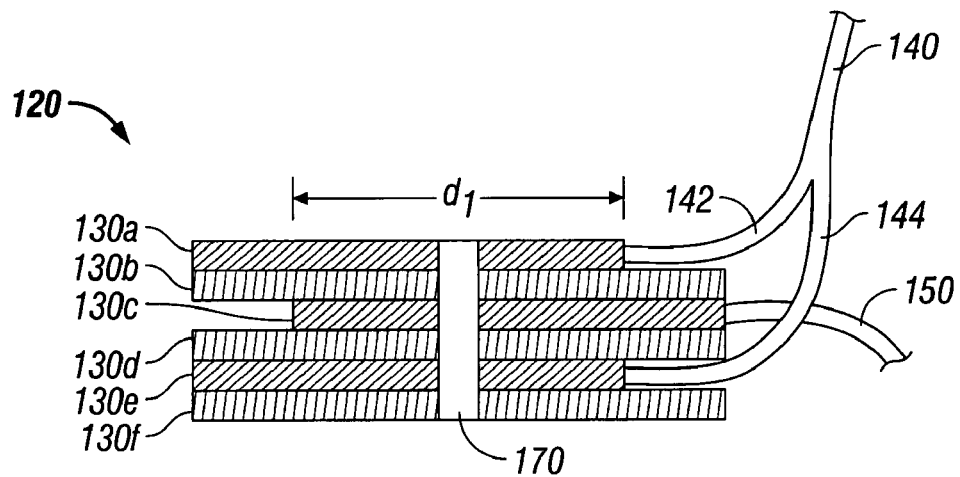
FIG. 3 is a cross-sectional view of a portion of the printed circuit board of FIG. 2.

With reference to FIGS. 2 and 3, printed circuit board 120 includes a plurality of layers 130. Layers 130 are shown having enlarged thicknesses for clarity. Specifically, layers 130 of printed circuit board 120 include at least a first conductive layer 130a, a first dielectric layer 130b, a second conductive layer 130c, a second dielectric layer 130d, a third conductive layer 130e and a third dielectric layer 130f as illustrated. In particular, as seen in FIG. 2, first dielectric layer 130b is shown interposed between first conductive layer 130a and second conductive layer 130c of printed circuit board 120. Second dielectric layer 130d is shown interposed between second conductive layer 130c and third conductive layer 130e of printed circuit board 120. Third dielectric layer 130f is shown adjacent third conductive layer 130e.

Electrosurgical generator 110 includes a generator ground 140 electrically connected to printed circuit board 120. Generator ground 140 includes at least a first portion 142 and a second portion 144. First portion 142 of generator ground 140 may be electro-mechanically connected to a conductive layer (e.g., first conductive layer 130a) of printed circuit board 120. Second portion 144 of generator ground 140 may be electro-mechanically connected to a different conductive layer (e.g., second or third conductive layer 130c or 130e) as compared to first portion 142.

Electrosurgical generator 110 further includes a patient ground 150 that is electro-mechanically connected to a conductive layer (e.g., second conductive layer 130c). Patient ground 150 may be at least partially interposed between first portion 142 of generator ground 140 and second portion 144 of generator ground 140.

As can be appreciated, both generator ground 140 and patient ground 150 are configured to allow an electrical current to flow therethrough. The currents include a frequency having a particular wavelength. As illustrated in FIG. 3, it is envisioned that at least two adjacent conductive layers (e.g., first conductive layer 130a and second conductive layer 130c) of printed circuit board 120 overlap one another by at least a distance "$d_1$," equaling about ¼ of one wavelength of the electrical current flowing from generator ground 140 and/or patent ground 150. In one particular embodiment, distance "$d_1$" may be about 4.0 inches (10.16 cm). The overlapping of adjacent conductive layers (e.g., conductive layers 130a, 130c) helps minimize various losses incurred by generator ground 140 and/or patient ground 150, particularly with respect to their use in microwave generators with frequencies of more than about 500 MHz.

Figure 4:
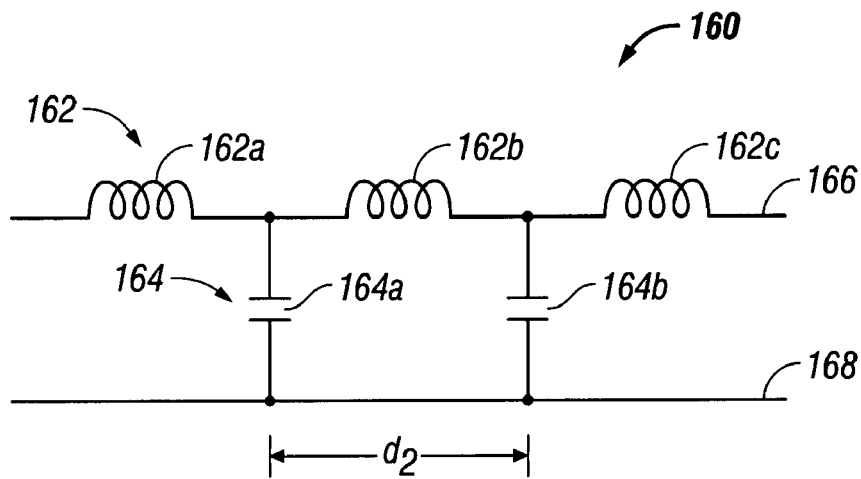
FIG. 4 is a schematic view of microstrip lines of the printed circuit board of FIGS. 2 and 3.

According to various embodiments of the present disclosure, illustrated in FIG. 2 and schematically in FIG. 4, printed circuit board 120 may include a microstrip 160 disposed in mechanical cooperation with a surface thereof. Microstrip 160 facilitates a user's ability to tune printed circuit board 120 to help optimally reduce losses incurred by generator ground 140 and/or patient ground 150. For example, lengths and/or widths of an active line 166 (e.g., disposed in electro-mechanical cooperation with microwave ablation device 200 and configured to transmit energy to microwave ablation device 200) and/or microstrip 160 can be varied to help tune printed circuit board 120. It is envisioned that microstrip 160 is between about 0.0787 inches (2.00 mm) and about 0.0827 inches (2.10 mm) wide and, in an embodiment, may be about 0.0807 inches (2.05 mm) wide. In an embodiment, where microstrip 160 is about 0.0807 inches (2.05 mm) wide, the impedance may equal about 27.3 ohms and its length may be about 2.5 inches (63.5 mm). Microstrip 160 may have a thickness equal to about the thickness of copper (about 70 μm or 2.7 mils) plus the thickness of any dielectric associated therewith (about 0.5 mm to about 1.5 mm or about 20 mils to about 60 mils. Microstrip 160 may be constructed of a suitable electrically conductive material, such as, for example copper, silver, and/or gold.

Microstrip 160 may be schematically illustrated in FIG. 4 to include at least one inductor 162 and at least one capacitor 164, such that the characteristic impedance (I) of the transmission line may be represented by:

$$I = \sqrt{\frac{inductor}{capacitor}}$$

As seen in FIG. 4, microstrip 160 is shown including three inductors 162a, 162b, 162c connected in series, two capacitors 164a, 164b connected in parallel between inductors 162a, 162b, 162c, an active line 166 and a ground line 168. It is envisioned that capacitors 164a and 164b are separated by a distance "$d_2$", which may be about 2.3622 inches (60 mm).

Figure 5:
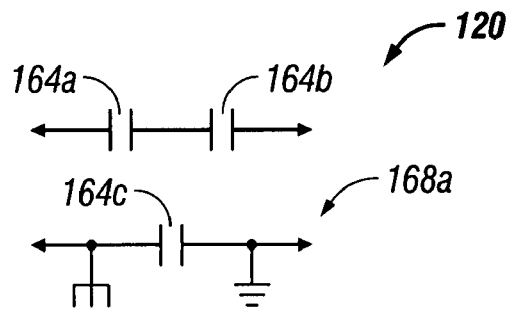
FIG. 5 is a schematic view of an electrical component of the printed circuit board of FIGS. 2 and 3.

With reference to FIG. 5, ground line 168a represents the coupling between generator grounds 140 and patient ground 150, where capacitor 164c represents the sum of capacitance coupling between first portion 142 of generator ground 140 and patient ground 150, and between second portion 144 of generator ground 140 and patient ground 150.

As illustrated, printed circuit board 120 may include a plurality of vias 170 disposed at least partially therethrough (FIGS. 2 and 3). Specifically, printed circuit board 120 of FIG. 2 is shown having vias 170 disposed at various locations around printed circuit board 120 and in a predetermined arrangement. FIG. 3 illustrates a cross-section of a portion of printed circuit board 120 taken through a singe via 170. It is envisioned that vias 170 electrically connect first portion 142 of generator ground 140 with second portion 144 of generator ground 140. In a disclosed embodiment, a plurality of vias 170 are spaced less than approximately 15° of a wavelength from adjacent vias 170; for example a first via 170a is spaced less than approximately 15° of a wavelength from an adjacent second via 170b (See FIG. 2). A via pattern 170c is configured such that vias 170 at least partially surround patient ground 150, thus helping to increase the coupling between generator ground 140 and patient ground 150. Additionally, the spacing of via pattern 170c from patient ground 150 may be electrically separated to ensure a relatively high dielectric standoff between patient ground 150 and generator ground 140 at relatively low frequencies (approximately 60 Hz, for instance). Further, the spacing of vias 170 is configured to encompass patient ground 150 in an electrical box. That is, a top portion and a bottom portion of patient ground 150 are each coupled to first portion 142 and second portion 144 of generator ground 140 and a side portion of patient ground 150 is coupled to plurality of vias 170.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

What is claimed is:

1. An electrosurgical system for treating tissue, the system comprising:
an electrosurgical generator;
a printed circuit board disposed in electro-mechanical cooperation with the electrosurgical generator, the printed circuit board including a plurality of conductive layers;
a generator ground including a first portion and a second portion, the first portion of the generator ground electro-mechanically connected to a first conductive layer of the plurality of conductive layers and the second portion of the generator ground electro-mechanically connected to a second conductive layer of the plurality of conductive layers; and
a patient ground including a portion electro-mechanically connected to a third conductive layer of the plurality of conductive layers, wherein the third conductive layer is at least partially interposed between the first conductive layer and the second conductive layer.

2. The electrosurgical system of claim 1, wherein the printed circuit board includes a dielectric layer interposed at least partially between the first conductive layer and the second conductive layer.

3. The electrosurgical system of claim 1, wherein the printed circuit board includes a first dielectric layer interposed between the first conductive layer and the third conductive layer and a second dielectric layer interposed between the second conductive layer and the third conductive layer.

4. The electrosurgical system of claim 1, wherein the generator ground includes a frequency having a wavelength and the patient ground includes a frequency having a wavelength, and wherein at least two adjacent conductive layers of the printed circuit board overlap one another by about ¼ of one wavelength of at least one of the generator ground and the patient ground.

5. The electrosurgical system of claim 1, wherein at least two adjacent conductive layers of the printed circuit board overlap one another by about four inches.

6. The electrosurgical system of claim 1, wherein the printed circuit board includes a microstrip disposed in mechanical cooperation with a surface thereof.

7. The electrosurgical system of claim 1, wherein the electrosurgical generator is configured to supply energy having a frequency greater than about 500 MHz.

8. The electrosurgical system of claim 1, wherein the patient ground is electro-mechanically connected to at least one of a microwave ablation device, a patient pad and an electrosurgical ablation device.

9. The electrosurgical system of claim 1, wherein the printed circuit board includes a plurality of vias disposed at least partially therethrough.

10. The electrosurgical system of claim 9, wherein spacing between adjacent vias of the plurality of vias is less than about 15°.

11. The electrosurgical system of claim 1, further including a microwave ablation device including an active line configured to deliver energy, at least a portion of the active line is disposed in electro-mechanical cooperation with the printed circuit board.

12. The electrosurgical system of claim 11, wherein the active line is a transmission line having an impedance of about 50Ω.

13. The electrosurgical system of claim 11, further including a first capacitor and a second capacitor disposed in mechanical cooperation with the active line, the first capacitor and the second capacitor being configured to isolate the active line.

\* \* \* \* \*